(12) United States Patent
Kennedy (10) Patent No.: US 8,133,189 B2
(45) Date of Patent: Mar. 13, 2012

(54) SYSTEM, DEVICE AND METHOD FOR ASSESSING TACTILE SENSORY DEFICIT

(75) Inventor: William R. Kennedy, St. Paul, MN (US)

(73) Assignee: Daniel L. M. Kennedy, Minneapolis, MN (US)

( * ) Notice: Subject to any disclaimer, the term of this patent is extended or adjusted under 35 U.S.C. 154(b) by 527 days.

(21) Appl. No.: 12/030,763

(22) Filed: Feb. 13, 2008

(65) Prior Publication Data
US 2012/0035497 A1    Feb. 9, 2012

(51) Int. Cl.
*A61B 19/00*    (2006.01)
(52) U.S. Cl. ....................................................... 600/557
(58) Field of Classification Search ................... 600/557
See application file for complete search history.

(56) References Cited

U.S. PATENT DOCUMENTS

| | | | |
|---|---|---|---|
| 4,250,891 A * | 2/1981 | Carlson et al. | 600/557 |
| 5,011,413 A * | 4/1991 | Ferris et al. | 434/358 |
| 6,267,733 B1 * | 7/2001 | Peterson et al. | 600/587 |

OTHER PUBLICATIONS

Decker, Caroline et al., The Little Man Inside of Your Brain, Jan. 30, 2007, http://sleep25.vetmed.wsu.edu/KidsJudge2/KidsJudge2007.html, single page.*

LaMotte, Robert H. et al., Surface Microgeometry: Tactile Perception and Neural Encoding, 1991, Information Processing in the Somatosensory System Eds: O. Franzen and J. Westman, Wenner-Gren International Symposium Series, MacMillan Press, pp. 49-58.*

* cited by examiner

*Primary Examiner* — Max Hindenburg
*Assistant Examiner* — Emily Lloyd
(74) *Attorney, Agent, or Firm* — Schwegman, Lundberg Woessner, P.A.

(57) ABSTRACT

Various device embodiments comprise a substrate with a smooth surface, and a plurality of objects on the smooth surface. Each of the plurality of objects have a predetermined dimension capable of being sensed by a healthy person with a normal tactile sensory ability. Each of the plurality of objects have a different, predetermined dimension corresponding to distinct levels of tactile sensory ability.

25 Claims, 4 Drawing Sheets

GRADING INDICIA (E.G. SCALE 1- #)

SYSTEM, DEVICE AND METHOD FOR ASSESSING TACTILE SENSORY DEFICIT

TECHNICAL FIELD

This application relates generally to medical testing systems, devices and methods and, more particularly, to systems, devices and methods for assessing tactile sensory deficit.

BACKGROUND

Persons who have a deficiency of touch complain that commonly touched objects such as clothing, skin, dishes, steering wheel, toothbrush etc. do not feel "right". They have increased difficulty handling small, light objects like pins, pencils and buttons, which they cannot maneuver well and tend to drop. When the deficiency of touch is more advanced, they cannot feel objects like small pebbles in the shoes and develop blisters or skin wounds.

Other symptoms that may be experienced by persons with a deficiency of touch include numbness of toes, feet or other skin locations. Abrasions, burns, infections, disequilibrium or motor system problems can result when one is unaware of harmful stimuli. Abnormal touch sensation can be caused by disease or injury to the spinal cord, brain or peripheral nerves. Peripheral nerve damage may be caused by trauma to arms or legs or peripheral neuropathy associated with certain conditions such as diabetes, HIV, herpes (shingles), toxic substances and carpal tunnel.

If the person is diabetic there is a real threat of non-healing sores, gangrene and amputation. Diabetes is the world's most frequent cause of leg amputation, which essentially demobilizes the patient. In underdeveloped countries there is little chance for an amputee to earn a living. In order to decrease the incidence of amputations from diabetic neuropathy, it is important to make an early diagnosis of diabetic neuropathy and measure the degree of severity of the diabetic neuropathy. The length of time that neuropathy has occurred, as well as the degree of nerve fiber damage or loss, contribute to the creation of skin sores, infection and chances of eventual amputation. However, clinicians are not easily able to quantify a deficiency of touch sensation. This problem is compounded in underdeveloped countries.

One easy and fast classical neurological test for touch sensation involves lightly touching the skin with the examiner's fingers or a whisk of cotton and asking if the subject felt the stimulation or if the stimulation felt normal. Any body surface can be tested. However, the stimulus is not calibrated and the results are subjective, non-quantified and not repeatable. Another classical method to test touch sensation uses a calibrated set of "von Frey hairs" (sold commercially as Semmes-Weinstein nylon filaments) of known bending force. Individual nylon filaments are pressed one at a time onto the skin's surface until the filament bends. The threshold can be determined by detecting the filament of lowest bending force on more than 50% of trials. The test is time consuming for each site tested and is subjective. Vibration threshold is usually tested using a tuning fork of known vibration frequency placed on the affected skin and timing the seconds it is perceived. Responses to these stimuli are subjective.

More elaborate expensive devices measure touch threshold using single calibrated stimuli, usually a thin rod that indents the skin by a controlled and known distance with calibrated velocity in a direction perpendicular to the skin's surface. These are similar in principal but better calibrated than the Semmes-Weinstein nylon filaments. Factors that influence the detection of stimuli include the speed of skin indentation, size of stimulated area, amount of pre-indentation and characteristics of repetitive components, if present. Patient response is by forced choice response of whether the stimulus is felt or not felt. Such forced choice responses are time consuming, as a choice is made after each time the rod indents the skin. Several trials are necessary with different stimulus strengths to determine the threshold. These devices are sophisticated electro-magnetic devices that cost several thousand dollars, and require technical and computer support. Testing with these devices almost always requires a patient visit to a special laboratory. They are rarely used in the clinic or at the bedside, even in research institutions.

None of these techniques assess tactile sensory deficit for normal people or people suspected of having lost tactile sensory function by measuring the tactile capacity to detect irregularities on a surface when the surface is moving across the skin or when the skin is moving across the surface even though this is the common means that we humans use to detect or "feel" surfaces or objects.

Dr. Robert LaMotte researched the touch threshold of healthy humans and monkeys using raised dots or bumps of different sizes on otherwise smooth surfaces. Results were gathered from normal young subjects, without testing for variations due to age, sex and race. He did not measure the responses of persons with disease. This work identified an appropriate size and height of bumps on smooth surfaces that could be felt by a normal, healthy human. The work was performed in a controlled, research environment rather than in a practical situation such as a medical clinic or in the field for epidemiology. Measurements did not include the sensory function of the toes.

SUMMARY

Various device embodiments comprise a substrate with a smooth surface, and a plurality of objects on the smooth surface. The smooth surface is smooth to a touch of a person with a normal tactile sensory ability. Each of the plurality of objects on the smooth surface have predetermined dimensions capable of being sensed by the person with the normal tactile sensory ability. Each of the plurality of objects on the smooth surface have different, predetermined dimensions corresponding to distinct levels of tactile sensory ability.

According to various method embodiments, a subject is identified who has or is at risk of developing a tactile sensory deficit, and the patient is tested. Testing the subject includes requesting the patient to sense, using touch, for at least one object on a smooth surface of a substrate, where each object on the smooth surface has a predetermined dimension corresponding to a tactile sensory ability. Testing the subject further includes receiving an indication from the subject regarding the subject's ability to sense an object by identifying the location of the object. This provides an objective grade of tactile sensory deficit based on the indication from the subject. The object is placed in one of several locations that the subject is instructed to touch (feel). Success at locating the object in one of the several locations assures that the subject did not guess that the object was present. It allows testing to be completed with fewer trials than the forced choice method. Thus, the present subject matter saves time in providing accurate results over the forced choice method.

A system embodiment comprises a device and a computer system. The device includes a substrate with a smooth surface, and a plurality of objects on the smooth surface. The smooth surface is smooth to a touch of a person with a normal tactile sensory ability. Each of the plurality of objects have a predetermined dimension capable of being sensed by the person with the normal tactile sensory ability. Each of the plurality of objects also have a different dimension corresponding to distinct levels of tactile sensory ability. The computer system includes a data input to receive input regarding which of the plurality of objects are sensed by a patient, memory, and a processor adapted to communicate with the data input and the memory to store inputted data regarding which of the plurality of objects are sensed by the patient in the memory and provide an objective grade of tactile sensory deficit.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter is able to determine the threshold of touch sensation (lowest recognizable stimulus) on the pads of the fingers and toes (or other sensitive body locations). The stimuli used are small objects, referred to as "bumps", placed or formed upon an otherwise smooth surface which the subject feels with the plantar pad of the fingers, toes or other skin locations. A "smooth surface" is a surface that does not have bumps or other aberrations that are capable of being sensed by a normal human tactile sensation. The term smooth refers to what a person with a healthy sense of touch would consider smooth. For example, for a normal human, the threshold of sensing a 550 µm diameter coin-shaped object is approximately 2-3 µm. If either the diameter or height of the object is greater, the threshold is lower; and if either diameter or height of the object is smaller, the threshold is higher. For example, some embodiments form the smooth surface such that each irregularity on the smooth surface has a height less than half of the threshold height for sensing an object with a similar footprint to the irregularity on the smooth surface. The bumps may vary in shape and size. Other design constraints can be used to provide the substrate with the smooth surface, as perceived by a human with a normal sense of touch.

For example, some embodiments use frosted or ground glass for the substrate with the smooth substrate. Frosted or ground glass is made from normal glass sheets. Normal glass sheets have very smooth surfaces, where the surface roughness of normal glass is in the range of 1 nm. Frosted glass is made by using a polishing powder to roughen the glass surface, and the surface roughness depends on the size of the particles that make up the powder. For example, a 500 grit frosted glass is formed using polishing powder particles with a maximum diameter of 1/500 inch (around 50 microns). The RMS surface roughness of this frosted glass has been measured to be in the 1 to 2 micron range. Various embodiments herein use frosted glass to provide a substrate with a smooth surface. Other substrates can be used to provide a substrate with a desirably smooth surface.

In the fingers or toes the objects touched are mainly detected by specific sensory receptor organs called Meissner's corpuscles. The sensory information is rapidly conveyed by peripheral nerves to the spinal cord (eventually to the brain) by large diameter myelinated sensory nerves. Myelin is the fatty material wrapped around many nerves that enable rapid conduction of nerve impulses.

Various device embodiments have a surface upon which are placed individual embossed stimuli that consist of discrete raised objects ("bumps") of graded dimensions (e.g. plateaus, hemispheres, or pyramids) or a series of elongated raised objects (stripes or "speed bumps"), that are of differing heights, widths, and spacing. Individuals explore the surface to determine which of the individual or grouped stimuli are detectable. Tactile sensation occurs from indentation of the skin, and by excitation of sense organs. Bumps usually excite the sense organs called Meissner corpuscles, but in some circumstances e.g. closely spaced individual bumps or elevated rows, the bumps can excite Merkel's (or Merkel) corpuscles, hairs, or Pacinian corpuscles. Sensory threshold is defined as the dimension of the smallest "bump" or "speed bump" that can be detected. Test results reveal sensory nerve fiber dysfunction and provide an objective estimate of touch and vibration sensory deficit that often occurs with pathology of peripheral nerves.

The bumps are suited for testing the plantar surface of the fingers or toes because these skin surfaces are most commonly used to touch objects for identification and to manipulate objects. These skin surfaces contain many Meissner corpuscles. However, lips, nose, heel or other skin areas can also be tested and the information conveyed by different receptors.

The testing procedure used is a form of psychophysiological testing. For example, the subject attempts to detect the presence of a single small object "bump" on a smooth surface by rubbing the finger over the area. The bump may be of any shape or dimension e.g. coin-shaped, pyramidal, cubical, rectangular, spheres or other shape. An embodiment uses a substrate with a smooth surface embossed with coin-shaped bumps with a 550 μm diameter and of variable height from 2 μm to greater than 100 μm. When testing the finger or toe pad, the lowest possible threshold is obtained if the subject rubs the finger from side to side so that the edge of the bump strikes the raised ridge of the fingerprint at approximately 90 degrees. Since the Meissner corpuscles are located longitudinally in the raised print ridge, the side to side motion will activate the greatest number of corpuscles. The smallest bump detected is the threshold under the conditions of the testing. Several algorithms can be used. In the simplest algorithm the bumps are arranged in a row from smallest to largest in height and the subject feels from smallest to largest or vice versa. This establishes the approximate threshold in a few seconds. The necessary number of trials can be lowered if bumps are at random locations in a defined space area of a size that is practical to search within a few seconds. The subject then must locate the bump. This increases the certainty that the subjects actually felt the bump.

The main sensory organs in the skin to respond to touch are the Meissner corpuscles, which are mainly in the palms and soles, and are more concentrated on the pads of the fingers, toes, lips and a few other areas. Sheer forces and some aspects of touch are relayed by Merkel corpuscles. Touch on hairy skin is relayed by receptors on hair follicles and skin sensory organs called Merkel corpuscles. Vibration to repetitive stimulation are relayed mainly by the Pacinian corpuscles, which lie deeper in the skin around the joints and even in the peritoneal cavity round the gastrointestinal tract. Pacininian corpuscles respond to stimuli from a few cycles per second to over 1,000 cycles per second.

Figure 1A:
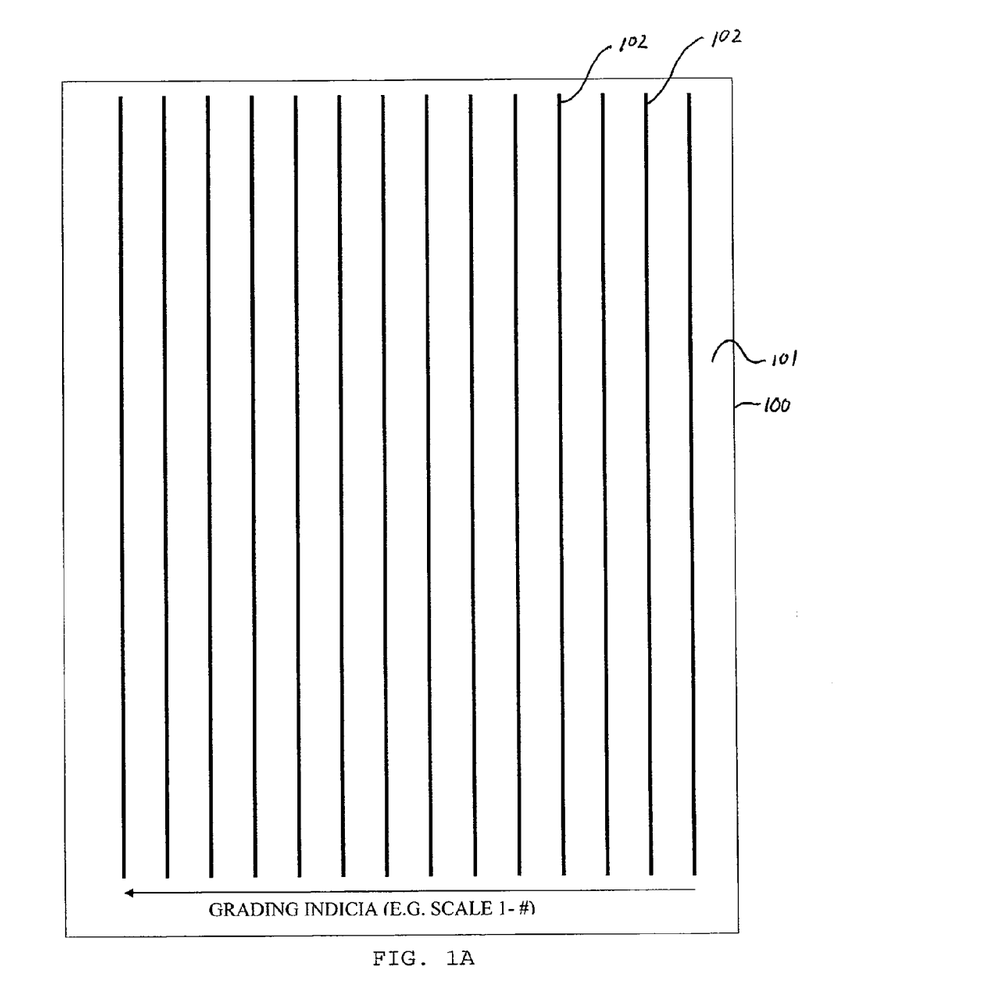
FIGS. 1A-1B illustrate top and side views of a device embodiment that includes raised rows to assess tactile sensory deficit.
Figure 1B:
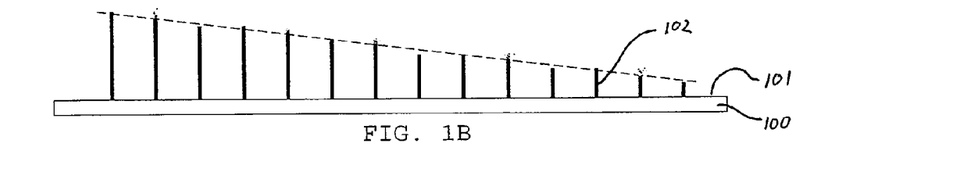

FIGS. 1A-1B illustrate top and side views of a device embodiment that includes raised rows to assess tactile sensory deficit. The illustrated device embodiment includes a substrate 100 with a smooth surface 101 with respect to a normal human tactile senses, and a predetermined number of objects 102 with predetermined dimensions that can be sensed by a normal human's tactile senses. In the illustration, the objects are arranged in rows. The objects can be formed, by way of example, as a raised line or ridge, as multiple distinct bumps arranged in rows, or as bumps fused to form lines. These rows are also referred to as "speed bumps."

The height, width and spacing of the rows 102 can be increased or decreased to adjust the detectability of the rows. For example, higher rows are more detectable than shorter rows. Also, the cross-sectional shape of the rows can be adjusted to adjust the sharpness of the edge of the rows. The spacing of the rows may be such to not only be detectable by Meissner corpuscles, but also to generate a stimulation frequency capable of being detected by Pacinian corpuscles when fingers or toes, for example, are rubbed across the rows.

The illustrated device illustrates that the rows are increased from a first, low height at a first end of the substrate to a second, high height at a second end of the substrate. The subject or patient can be asked to rub their finger from the first end to the second end, and identify on the substrate where they first felt a row. Grading indicia can be printed on the card to enable the patient or test giver to quantify and record where the patient first felt a row. Various grading indicia can be used, such as a scale from 1 to 10 or other number.

The objects or bumps on the smooth surface can be formed in a variety of shapes. For example, some embodiments form the objects or bumps by forming pillars. The following is a method for forming a substrate with a smooth surface and objects on the smooth surface. Other methods can be used. An embodiment uses frosted glass for the substrate, and cuts the glass into 1.5"×1.5" squares. In order to obtain a vacuum seal on the resist spinner chuck prior to spinning resist, the glass substrates are adhered to a silicon wafer with double-sided tape. After soft baking, the tape is removed from the backside with methyl ethyl ketone solvent. Photo-resist pillar structures are produced on these substrates, with each glass piece containing one pillar (550 pm diameter).

According to some embodiments, the objects on the smooth surface have a pillar like structure. The following illustrates methods for forming pillars with thicknesses of 3, 5, 6, 7, 8, 9, 12, 15, and 18 μm. The 3, 5, 7, and 9 μm pillars can be produced with positive resist. 9 μm pillars can be produced and subsequently etched with an oxygen plasma to yield 6 μm and 8 μm pillars. The 12, 15, and 18 micron pillars can be produced with a more robust negative resist (creating three ~20 μm pillars and subsequently etching them in an oxygen plasma until the desired thicknesses were obtained) to ensure adequate strength. More particularly, the following process can be used to form the pillars. The substrate is pre-cleaned in preparation to form the pillars. Pre-cleaning the substrate involves initially cleaning glass substrates with DI water, an isopropyl alcohol rinse, and an acetone rinse, and then blowing off the samples with $N_2$ to remove any residual solvent from cleaning.

A 3 μm pillar can be formed by pre-baking the substrate at 115° C. for 180 seconds, performing a HMDS (hexamethyldisilazane) vapor prime for 180 seconds, spinning SPR 220-4.5 at 6000 RPM for 35 seconds, softbaking at 115° C. for 180 seconds, exposing at 12 mW/cm$^2$ for 27 seconds, hardbaking at 115° C. for 180 seconds, and developing in CD-26 developer for 55 seconds.

A 5 μm pillar can be formed by prebaking the substrate at 115° C. for 180 seconds, performing a HMDS (hexamethyldisilazane) vapor prime for 180 seconds, spinning SPR 220-4.5 at 6000 RPM for 35 seconds, softbaking at 115° C. for 180 seconds, exposing at 12 mW/cm$^2$ for 27 seconds, hardbaking at 115° C. for 180 seconds, and developing in CD-26 developer for 55 seconds.

A 7 μm pillar can be formed by prebaking the substrate at 115° C. for 180 seconds, performing a HMDS (hexamethyldisilazane) vapor prime for 180 seconds, spinning SPR 220-7.0 at 3450 RPM for 35 seconds (initial ramp up to 500 RPM at 100 RPM/sec/sec), softbaking at 115° C. for 180 seconds, exposing at 12 mW/cm$^2$ for 39 seconds, hardbaking at 115° C. for 180 seconds after a 45 minute hold, and developing in CD-26 developer for 120 seconds.

A 9 μm pillar can be formed by prebaking a substrate at 115° C. for 180 seconds, performing a HMDS (hexamethyldisilazane) vapor prime for 180 seconds, spinning SPR 220-7.0 at 1900 RPM for 35 seconds, softbaking at 115° C. for 180 seconds, exposing at 12 mW/cm$^2$ for 45 seconds, hardbaking at 115° C. for 180 seconds after a 60 minute hold, and developing in CD-26 developer for 180 seconds.

A 6 μm pillar can be formed by forming a 9 μm pillar and etching the pillar to 6 μm. Forming a 9 μm pillar includes prebaking a substrate at 115° C. for 180 seconds, performing a HMDS (hexamethyldisilazane) vapor prime for 180 seconds, spinning SPR 220-7.0 at 1900 RPM for 35 seconds, softbaking at 115° C. for 180 seconds, exposing at 12 mW/cm$^2$ for 45 seconds, hardbaking at 115° C. for 180 seconds after a 60 minute hold, and developing in CD-26 developer for 180 seconds. Etching the pillar includes placing the glass substrate with a 9 µm pillar into a dry plasma etcher containing an oxygen plasma (100 sccm $O_2$, 100 mT process pressure, 100 W forward power) for 30 minutes to etch the resist at a rate of ~0.1 µm/min, thus yielding a 6 µm pillar.

An 8 µm pillar can be formed by forming a 9 µm pillar and etching the pillar to 8 µm. Forming a 9 µm pillar includes prebaking a substrate at 115° C. for 180 seconds, performing a HMDS (hexamethyldisilazane) vapor prime for 180 seconds, spinning SPR 220-7.0 at 1900 RPM for 35 seconds, softbaking at 115° C. for 180 seconds, exposing at 12 mW/cm$^2$ for 45 seconds, hardbaking at 115° C. for 180 seconds after a 60 minute hold, and developing in CD-26 developer for 180 seconds.

Etching the pillar includes placing the glass substrate with a 9 µm pillar into a dry plasma etcher containing an oxygen plasma (100 sccm $O_2$, 100 mT process pressure, 100 W forward power) for 10 minutes to etch the resist at a rate of ~0.1 µm/min, thus yielding an 8 µm pillar.

Pillars with heights of 13, 15, and 18 µm can be formed from 20 µm pillars. A 20 µm pillar can be formed by prebaking a substrate at 115° C. for 180 seconds, performing a HMDS (hexamethyldisilazane) vapor prime for 180 seconds, spinning SU-8 at 1100 RPM for 35 seconds (initial ramp up to 500 RPM at 100 RPM/sec/sec), softbaking at 115° C. for 240 seconds, exposing at 12 mW/cm$^2$ for 20 seconds, hardbaking at 115° C. for 240 seconds, and developing in PM Acetate developer for 180 seconds.

A 12 µm pillar can be formed by forming a 20 µm pillar, and etching the pillar to 12 µm by placing the glass substrate with a 20 µm pillar into a dry plasma etcher containing an oxygen plasma (100 sccm $O_2$, 100 mT process pressure, 100 W forward power) for 80 minutes to etch the resist at a rate of ~0.1 µm/min, thus yielding a 12 µm pillar.

A 15 µm pillar can be formed by forming a 20 µm pillar, and etching the pillar to 15 µm by placing the glass substrate with a 20 µm pillar into a dry plasma etcher containing an oxygen plasma (100 sccm $O_2$, 100 mT process pressure, 100 W forward power) for 50 minutes to etch the resist at a rate of ~0.1 µm/min, thus yielding a 15 µm pillar.

An 18 µm pillar can be formed by forming a 20 µm pillar, and etching the pillar to 18 µm by placing the glass substrate with a 20 µm pillar into a dry plasma etcher containing an oxygen plasma (100 sccm $O_2$, 100 mT process pressure, 100 W forward power) for 20 minutes. This process etched the resist at a rate of ~0.1 µm/min, thus yielding an 18 µm pillar.

After the substrate samples are formed with the pillars of the desired height, the samples can be subsequently adhered to a 4.5"×4.5" colored bump location grid using double-sided tape. The samples and attached grid can be adhered to a chromed glass plate for stability. A location key can be produced for the final product indicating the placement of all the pillars by thickness.

Those of ordinary skill in the art will appreciate, upon reading and comprehending this disclosure, that the substrate can be formed using a variety of materials and processes to form a surface that is smooth to the normal touch, and provide objects, bumps or aberrations of predetermined dimensions to test the sense of touch. By way of example and not limitation, lasers may be used to burn a series of cavities into appropriate material, and this material with the cavities can be used as a "negative" to form the substrate with the bump(s) by injection molding or other processes. It is desirable to use a method that provides test surfaces with reproducibly and accurately formed bumps to provide valuable, comparable data for each test of a patient over time, and each test of each patient in a population of patients.

Figure 2:
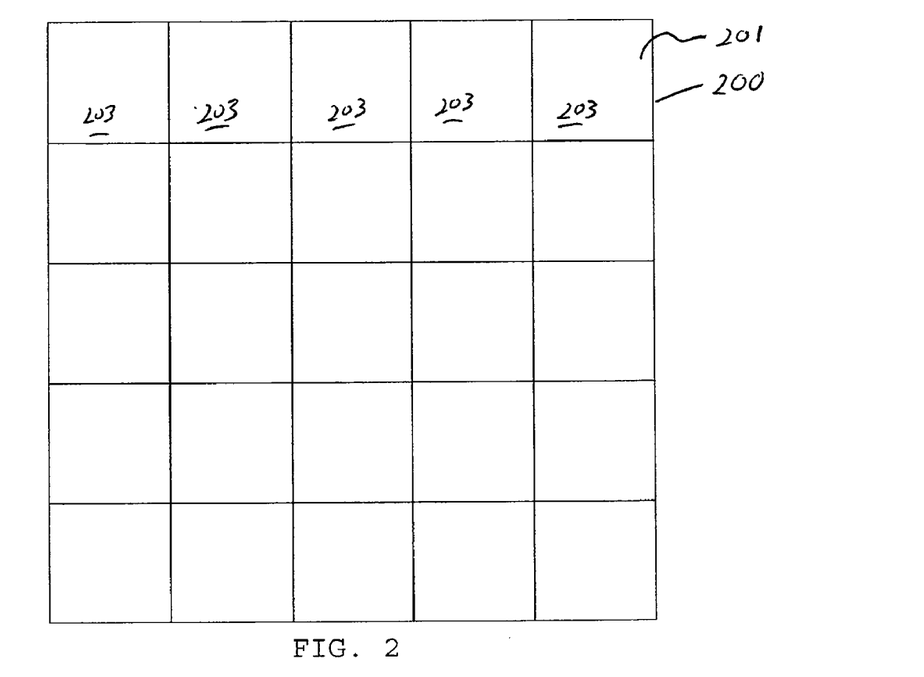
FIG. 2 illustrates a device embodiment with a plurality of test regions.

FIG. 2 illustrates a device embodiment with a plurality of test regions. The illustrated device includes a substrate 200 with a smooth surface 201. Each of the test regions 203 can be used to perform a separate test of tactile sensitivity (e.g. "Can you feel an object in this region?", and/or multiple regions 203 can be used in a single test of tactile sensitivity (e.g. "In which regions do you feel an object?"). For example, one test region can have objects that are more or less detectable than other test regions. Test regions may also have objects that are equally detectable, so as to provide additional assurances that the patient felt the object and did not guess that an object was felt. The illustrated number of test regions is 25, and each test region is illustrated as a square arranged in a matrix of rows and columns. The present subject matter is not limited to a particular number of test regions or to a particular shape, size or arrangement of test regions. The test regions are identified (e.g. color or label) such that a patient can be instructed to search a particular test region for an object, and/or indicate the test regions(s) where the patient detected an object. The results of the test allow one to assess the tactile sensing disability of the patient by identifying the bumps that a normal patient could feel but that a tested patient is unable to feel. Also, the test can be used to monitor changes in a patient's ability to sense bumps, which can be used to monitor the progression of a disease or therapy results.

Figure 3:
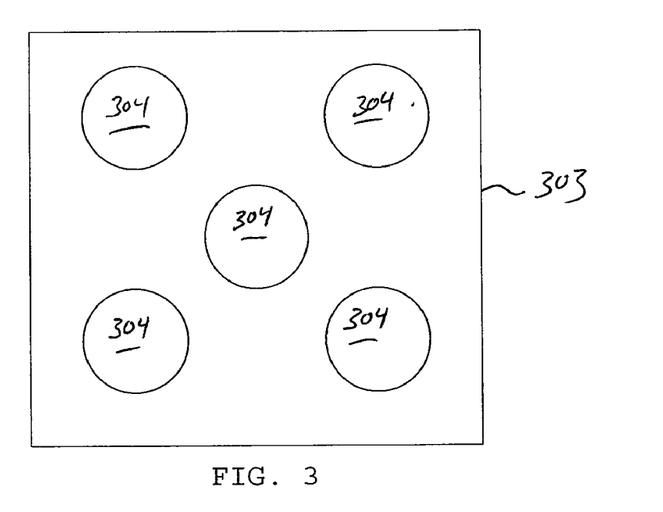
FIG. 3 illustrates a test region for a device embodiment, where the test region includes a plurality of visually-identifiable regions.

FIG. 3 illustrates a test region 303 for a device embodiment, where the test region includes a plurality of visually-identifiable regions 304. In an embodiment where the test region is about 1 inch by 1 inch, the visually-identifiable regions may be on the order of about ¼ inch by ¼ inch. The present subject matter is not limited to a particular number of visually-identifiable regions or to a particular shape, size or arrangement of test regions. A particular design can balance the statistical probabilities of guessing a correct answer against the increased complexity and decreased speed for performing the test. The visually-identifiable regions allow a patient to actively search a specific area of the substrate surface and identify where the object was detected. The visually-identifiable regions are illustrated as circles, but can be squares, triangles, etc. The regions can be identified by colors, lettering or numbering, shading, and the like. An embodiment uses markings chosen to camouflage the object on the surface to prevent or make it more difficult for a patient to visually identify the location of the objects on the surface. For example, a pattern of distinct images may be imprinted in each region 304, where each distinct image has the size and shape of a footprint of an object on the surface.

A test embodiment, such as may be used to test sensation in fingers, includes a substrate (e.g. card) having a smooth surface with nine 1 inch×1 inch squares arranged as in a tic-tac-toe game. Each square has 5 marked areas such as 5 circles, each identified by some marking, e.g. by a different color. The test object is a 550 µm diameter coin shaped disk (bump or object) that varies in height (thickness) between 2 and 100 µm or greater. One bump is placed on one of the 5 circles in each square, i.e. one bump/square. The subject touches each circle in a square in turn for a few seconds and identifies if and in some embodiments where a bump is located then progresses to the next square. Objects and test regions of various sizes can be used. For example, embodiments to test foot/toe sensation can have different sized objects and test regions.

Figure 4:
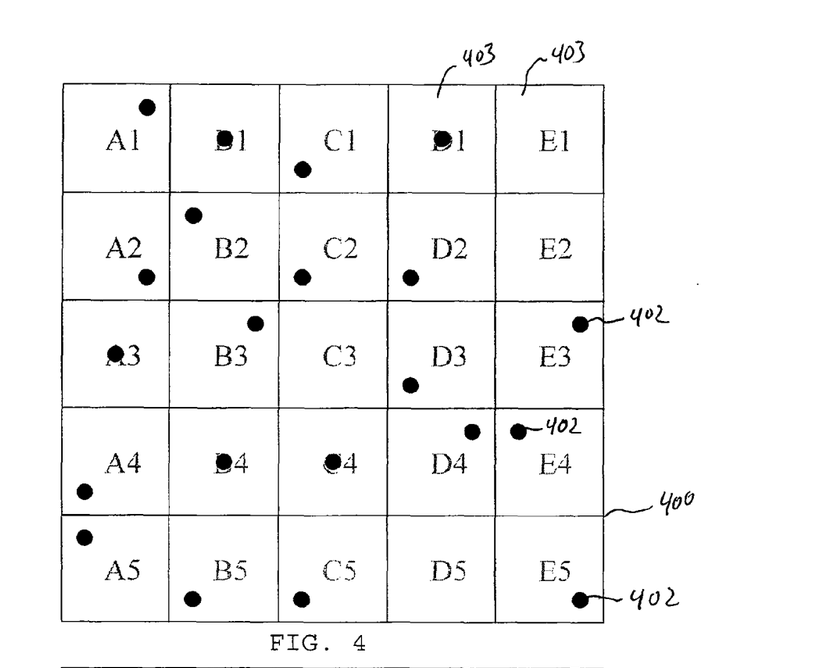
FIG. 4 illustrates an example of bump locations for a test using the device embodiment illustrated in FIGS. 2-3.

FIG. 4 illustrates an example of bump locations for a test using the device embodiment illustrated in FIGS. 2-3. The illustrated substrate 400 includes 25 squares, as an example, that function as test regions 403. More or fewer squares can be used. For example, one embodiment uses nine test areas arranged in 3 columns and 3 rows of squares. The visually-identifiable areas are not illustrated to simplify the illustration. The illustrated embodiment can have a bump, represented by the filled-in circle 402, in any of five locations in the test area (square). These five locations are center, upper left, upper right, lower left and lower right. Each of these five locations can be identified by a color or other indicia.

The patient can be requested to search test area A1 for a bump, which has dimensions associated with a predetermined tactile sensing ability. Some embodiments move the surface of the test area A1 across the patient's skin. If the patient indicates that the bump is in the upper right portion of the test area, it is recorded that the patient likely felt this bump and has the predetermined tactile sensing ability associated with the bump. Other test areas can have a bump with the same dimensions to reduce the statistical likelihood that the patient guessed the location of the bump rather than sensed the bump at the location. Additionally, other test areas can have bumps with other dimensions that are associated with other tactile sensing abilities (more or less sensing ability). The results of the test allow one to assess the tactile sensing disability of the patient by identifying the bumps that a normal patient could feel but that a tested patient is unable to feel. Also, the test can be used to monitor changes in a patient's ability to sense bumps, which can be used to monitor the progression of a disease or therapy results.

Figure 5:
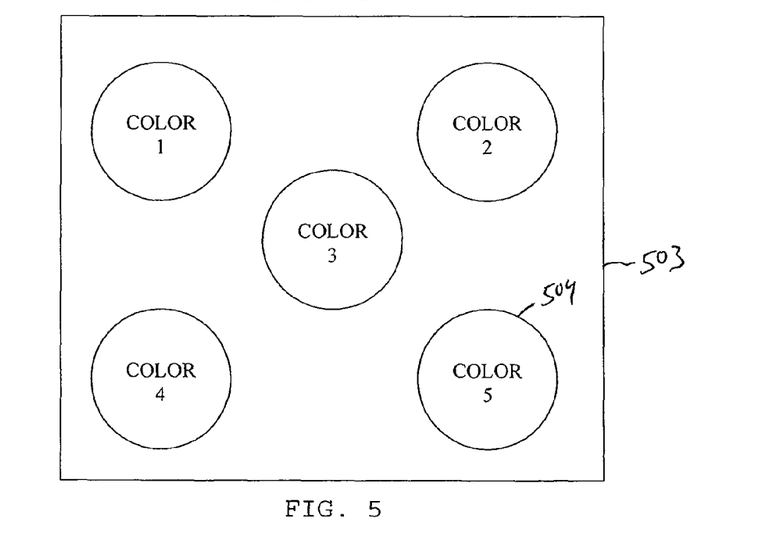
FIG. 5 illustrates a device embodiment that uses color to identify the visually-identifiable regions.

FIG. 5 illustrates a device embodiment that uses color to identify the visually-identifiable regions 504 in a test area 503. Shading, numbers and/or text may also be used to identify these regions in the test area. Scoring can be accomplished in several ways. A patient may verbally identify to the examiner whether a bump was felt, and the examiner can record the results as the test is given. A computer interface can be used for a patient to self-score or for a technician to score the test results in real time. A hand-held user friendly computerized system can be used to collect the data. The examiner or the tested subject can mark the location of each bump as they are identified on a card the same size and pattern as the tic-tac-toe test device. These can later be entered into a computer or hand held computer pad for storage and report generation. The test can be repeated by turning the test board 180 degrees if it is marked for identification with the same pattern or different sized bumps.

Figure 6:
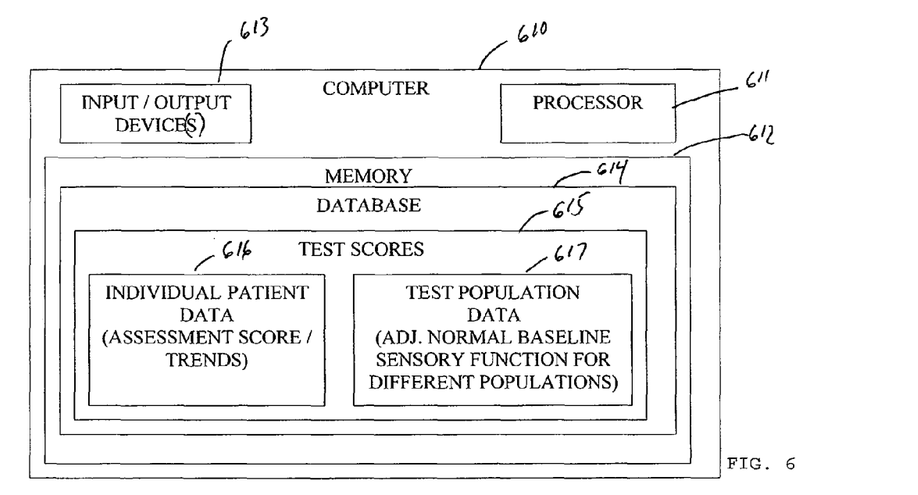
FIG. 6 illustrates a system embodiment for recording results of tests to assess tactile sensory deficit.

FIG. 6 illustrates a system embodiment for recording results of tests to assess tactile sensory deficit. The illustrated system embodiment 610 is a computer with a processor 611, memory 612 and input/output device(s) 613. The processor operates on instructions stored in the memory to perform various functions. The input/output devices can include, according to various embodiments, devices such as a keyboard, mouse, display, touch pad, touch screen display, and the like. The processor communicates with the data input and the memory to store inputted data regarding which of the plurality of objects are actively sensed by the patient in the memory and provide an objective grade of tactile sensory deficit. The memory includes a database 614, and the database includes test scores 615.

Because the present subject matter is to provide objective, reproducible scores, and to store these objective, reproducible scores for individual patients and various patient populations, the present subject matter is able to provide valuable statistical analysis of this data. For example, tests corresponding to one patient can be used to monitor disease progression and therapy results, and can be used to diagnose a pathological condition that is likely attributable to exposure to a nerve toxin or to a disease, or diagnose a localization of a nerve injury or nerve involvement (e.g., carpal tunnel syndrome, various trauma, pinched nerves, herniated disk, ischemic nerve, irradiation damaged nerve). For example, a local nerve injury would be suspected if only one hand of the patient experiences diminished sensation in the known sensory distribution of the nerve. Also, by way of example and not limitation, tests corresponding to a plurality of patients can be categorized using a number of patient criteria to define various patient populations. For example, data regarding the age, gender, race, height, weight, health, body mass index, geographical location, occupation, etc. of each patient can be associated with the scores. This information can be used to identify the "normal tactile sensation" for various populations (e.g. 70 year old male construction worker v. 5 year-old kindergarten student), and also to provide quantifications for sensory deficit for these populations (e.g. X % of population senses a bump with the height of M microns, and Y % of population senses a bump with the height of N microns).

The database can include individual patient test data 616, such as the assessment score for a particular test, and a scoring trend for the patient. The trend may reflect whether the touch sensation of the patient is improving, worsening, or staying the same. This data may be useful to monitor the progression of a disease or therapy results. The individual patient test data can include results for a particular skin area (e.g. a particular toe or finger). The assessment for a particular area of the patient can be compared to other areas of the patient to determine if the various areas compare normally to each other. The database can include data for a test population 617. This data can be used to monitor the effects and the extent of an exposure (e.g. radioactive exposure) to a population. Based on statistical analysis of test results for a population, this data can indicate that a patient in the population likely has been exposed to a neural toxin, for example. For example, rather than monitor for relatively few, known nerve toxins, a factory can routinely monitor the touch sensation of its employees (or a school can routinely monitor the touch sensation of its students and staff) to detect abnormalities that could lead to discovery of exposure to known or unknown nerve toxins before clinical manifestations of the exposure are observed. Such quick and objective monitoring could be used to test people who are in the area of an explosion, nuclear power plant, meat processing facility, etc. or an unknown substance.

This data can also be used to adjust the normal baseline for various population groups, and for different areas of the body (e.g. a particular finger, a particular toe, or other sensitive body part). For example, it is expected that that a normal ten-year-old has different tactile sensory function than a normal eighty-year-old, and that a foot is less sensitive than a finger pad. Thus, the normal tactile sensory function can be identified for different body parts and for different populations, thus accounting for differences such as differences in age and gender and other physical or mental features. Various quantification thresholds can be developed for these different populations and different body parts. Historical data can be used to develop criteria for determining if a particular therapy is indicated for a particular quantified sensation. As such, the objective and reproducible data may be used to identify a therapy indicated for a particular quantification of sense.

Figure 7:
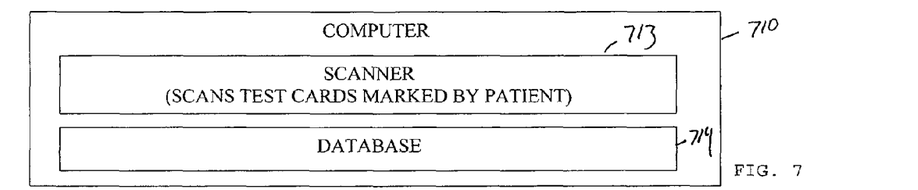
FIG. 7 illustrates a system embodiment with a scanner input for recording results of tests to assess tactile sensory deficit.
Figure 8:
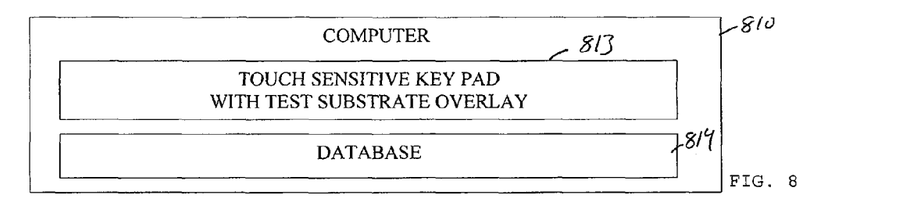
FIG. 8 illustrates a system embodiment with a touch sensitive key pad and test substrate overlay used to record results of tests to assess tactile sensory deficit.
Figure 9:
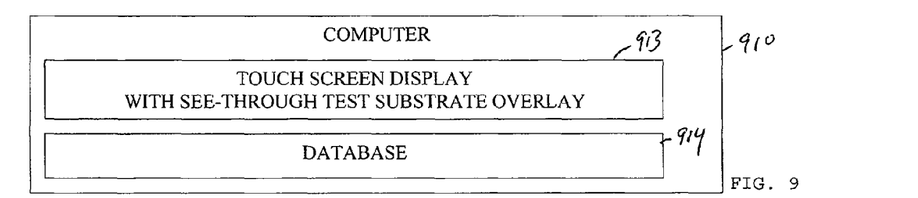
FIG. 9 illustrates a system embodiment with a touch screen display and a transparent test substrate overlay used to record results of tests to assess tactile sensory deficit.

The database can be used to correlate the test results to patient data (e.g. diabetic glucose control, age, etc.) and environmental data (e.g. nerve toxin exposure). The database can be populated with the test results manually after or while the test is being taken. The embodiments illustrated in FIGS. 7-9 are examples of systems where the population of the database is at least partially automated. These embodiments involve a cost-benefit assessment, as they trade the inexpensive card-type substrate with a more expensive computer system with an automated data input.

FIG. 7 illustrates a system embodiment 710 with a scanner input 713 for recording results of tests to assess tactile sensory deficit. The illustrated system is a simplified illustration of the system of FIG. 6. The scanner functions as an input/output device used to populate the database 714. A patient or an examiner marks the locations on the card where the patient identified a bump. The scanner identifies these markings on the card, and determines whether or not the markings correctly correspond to the actual locations of the bumps for scoring the results.

FIG. 8 illustrates a system embodiment 810 with a touch sensitive key pad and test substrate overlay 813 used to record results of tests to assess tactile sensory deficit. The illustrated system is a simplified illustration of the system of FIG. 6. The illustrated system includes a touch sensitive key pad that functions as an input to the computer system used to populate the database 814. The test substrate is sufficiently thin and flexible to function as an overlay to the key pad. The test substrate is appropriately registered on the key pad, such that each area where a bump may be found on the test substrate corresponds to a predetermined key on the key pad. A patient can tap or touch the location where the bump is felt. The key pad is able to detect the tap through the flexible substrate, and identify the location where the patient felt the bump.

FIG. 9 illustrates a system embodiment 910 with a touch screen display and a transparent test substrate overlay 913 used to record results of tests to assess tactile sensory deficit. The illustrated system is a simplified illustration of the system of FIG. 6. The test substrate is sufficiently thin, flexible and transparent to function as an overlay to the touch screen display. The touch screen display can provide the visually-identifiable areas, grading indicia and instructions for the test. The test substrate is appropriately registered on the touch screen display, such that each area where a bump may be found on the test substrate corresponds to a predetermined location on the touch screen display. A patient can tap or touch the location where the bump is felt. The touch screen display is able to detect the tap through the flexible substrate, and identify the location where the patient felt the bump. The identified location is populated into the database 914.

Modifications can be made to the arrangement, size and shape of the test objects or of the material used to construct the bumps or the underlying smooth surface. With computer application it can be used as the fundamental basis of educational games at home and school. The setting does not need to be a medical one. Testing can be done at industrial plants where there is a suspicion of toxic exposure and well as in war zones where troops are now in danger of exposure to neurotoxic materials.

The present subject matter can be used, according to various embodiments, to test persons with pathological conditions, such as carpal tunnel syndrome, diabetic neuropathy, burning legs syndrome, HIV neuropathy, neuropathy from chemotherapy, and many other conditions as opposed to testing normal persons for threshold values. Testing will be valuable for diagnosis and for following the progression of the condition and the effects of treatment. For example, the present subject matter can be used to monitor the efficacy of a prophylactic or therapeutic treatment.

The present subject matter provides a cost effective, rapid, quantitative, and reproducible tests of sensitivity of the important touch surfaces i.e. finger and toe pads. Some test device embodiments are small (e.g. pocket sized) and do not have moving parts. The size, portability, simplicity, and rapidity of use allow a physician, technical or lay person to easily carry the test device or system for use in the clinic, hospital, or any other location. The sensory threshold of the affected area can be measured in minutes at low cost. Thus, by way of example, an application for the present subject matter is epidemiology studies in either urban or primitive settings. This present subject matter is a fast easy means to test these diabetic (and other) patients for neuropathy that can be done by minimally trained persons or often by the patient themselves. The present subject matter can also be used in epidemiological studies of large populations in developed and underdeveloped countries as well as in clinic and hospital settings. Groups of subjects can be tested simultaneously because each subject can score his/her results. This makes it practical for use in epidemiology studies of large numbers of individuals, as for example people living in the radius of a factory suspected of emitting chemicals that cause nerve damage; large families in which a hereditary neuropathy affects many individuals, or troops and civilians exposed to nerve toxins or nuclear radiation.

Various embodiments involve a patient actively exploring test regions for surface features to assess tactile acuity or discrimination. Various embodiments rub a test region against the patient's skin to determine if the patient is able to sense an object as it moves against the patient's skin.

The present subject matter provides a rapid, accurate method to measure the threshold and acuity of human touch and vibration sensations for diagnosis of peripheral nerve disease or dysfunction, regardless of cause. The method is applicable for testing subjects with suspected decreased sensation or numbness resulting in difficulty handling small objects like pins and buttons. Various device embodiments can be used by minimally trained persons to monitor development, or progression of neurogenic disorders e.g. carpal tunnel syndrome, neuropathy from diabetes of other diseases or from chemotherapy. The present subject matter can also be used for grading disability (e.g. workman's compensation, personal injury law suits). The present subject matter provides a rapid, accurate test to determine with certainty if a deficit of touch sensation is present, and to identify its distribution and severity. Even when a disease of peripheral nerves (neuropathy) is present or after known trauma to an extremity, the presence and severity of a sensory deficit for touch is impossible to determine with accuracy. It is important to have an objective measure of touch sensation to diagnose and grade the presence of neuropathy for diagnosis, to guide therapy, to judge the response to treatment and to verify and score claims for compensation of industrial injuries. Psychological responses to workman's compensation or legal issues often complicate such situations.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. For example, the present subject matter can be used to provide objective measures of a subject's tactile sensory ability, whether the patient has a tactile sensory deficit (below a normal tactile sensory ability) or an enhanced tactile sensory ability (above a normal tactile sensory ability). The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method, comprising:
    identifying a subject who has or is at risk of developing a tactile sensory deficit; and testing the subject, including:
    requesting the subject to explore, using touch, a smooth surface to feel for and find an object on the smooth surface by rubbing a plantar pad of a finger or toe of the subject over the smooth surface, wherein the object on the smooth surface has characteristics that prevent or make it difficult to visually locate the object, the object is at a location on the smooth surface unknown to the subject before the subject feels for the object, and each object on the smooth surface has a predetermined dimension corresponding to a tactile sensory ability;
    receiving an indication from the subject indicating whether the subject found the object; and
    providing an objective grade of tactile sensory deficit based on whether the subject correctly found the object where the object is located on the smooth surface.

2. The method of claim 1, wherein requesting the subject to explore the smooth surface includes requesting the subject to actively search a smooth surface of a card.

3. The method of claim 2, wherein:
    the card includes a plurality of objects and a plurality of visibly identifiable regions on the smooth surface; and
    requesting the subject to explore includes requesting the subject to explore each of the plurality of visually identifiable regions on the card; and
    receiving the indication includes receiving from the subject an identification of the visibly identifiable regions in which the subject found one of the plurality of objects.

4. The method of claim 2, wherein:
    the card includes a plurality of test regions, and each test region includes a plurality of objects and a plurality of visibly identifiable regions on the smooth surface; and
    requesting the subject to explore includes requesting the subject to explore each of the plurality of visually identifiable regions in each test region on the card; and
    receiving the indication includes receiving from the subject an identification of the visually identifiable regions in which the subject found one of the plurality of objects.

5. The method of claim 1, wherein receiving the indication from the subject includes receiving a tap from the subject on a touch sensitive input device.

6. The method of claim 5, wherein the surface is a surface of a substrate and the substrate is an overlay on the touch sensitive input device, wherein receiving an indication from the subject includes detecting a tap on the substrate utilizing the touch sensitive input device.

7. The method of claim 1, including:
    testing the subject at a plurality of times to provide an objective grade of tactile sensory deficit at each of the plurality of times; and
    trending the objective grades for the subject.

8. The method of claim 1, wherein:
    each object has a predetermined size and shape corresponding to a quantified ability to sense the object by touch; and
    providing the objective grade of tactile sensory deficit includes reading a visually-perceptible identifier on the smooth surface corresponding to a region where the subject felt for the object.

9. The method of claim 1, wherein providing the objective grade of tactile sensory deficit includes identifying a distribution and severity of tactile sensory deficit for a test population.

10. A device, comprising:
    a substrate with a smooth surface that is smooth to a touch of a person with a normal sensory ability; and
    a plurality of objects on the smooth surface, each of the plurality of objects having a predetermined dimension capable of being sensed by the person with the normal tactile sensory ability when the person with the normal tactile sensory ability rubs a plantar pad of a finger or toe over the smooth surface of the substrate, each of the plurality of objects on the smooth surface having characteristics that prevent or make it difficult to visually locate the objects, each of the plurality of objects further having a different, predetermined dimension corresponding to distinct levels of tactile sensory ability for use in determining the tactile sensory deficit of the test subject.

11. The device of claim 10, wherein each object on the smooth surface has a disc shape with a diameter of approximately 550 μm and a predetermined height within a range of approximately 2 μm to at least 100 μm, each predetermined height corresponding to a tactile sensory ability.

12. The device of claim 10, wherein the objects on the smooth surface have varied sizes or varied shapes.

13. The device of claim 10, wherein the objects on the smooth surface include lines or ridges of varied heights.

14. The device of claim 10, wherein the objects on the smooth surface have a shape selected from a group of shapes consisting of: coin-shaped, pyramidal, cubical, rectangular, and spherical.

15. The device of claim 10, wherein the smooth surface includes a plurality of visually-identifiable regions that are configured to be visually-identified by the test subject, at least one of the visually-identifiable regions including one of the objects that has a predetermined dimension corresponding to a level of tactile sensitivity.

16. The device of claim 10, wherein the smooth surface includes a plurality of test regions, each of the test regions including a plurality of visually-identifiable regions that are configured to be visually-identified by the test subject, at least one of the visually-identifiable regions in each test region including one of the objects that has a predetermined dimension corresponding to a level of tactile sensitivity.

17. The device of claim 10, further comprising a touch-sensitive input device to a computer, wherein the substrate is sufficiently thin and flexible to be an overlay on the touch-sensitive input device, wherein the touch-sensitive input device and the substrate are configured to allow the test subject to touch the substrate to indicate a selection to the computer utilizing the touch-sensitive screen.

18. The device of claim 17, wherein the substrate is sufficiently transparent to allow the test subject to see visual identifiers displayed on using the touch-sensitive screen through the substrate.

19. The device of claim 10, wherein the substrate is a touch-sensitive input device to a computer.

20. The device of claim 10, wherein at least one object on the smooth surface has a height of 3 µm, 5 µm, 6 µm, 7 µm, 8 µm, 9 µm, 12 µm, 15 µm or 18 µm.

21. A system, comprising:
a device, comprising:
  a substrate with a smooth surface that is smooth to a touch of a person with a normal tactile sensory ability; and
  a plurality of objects on the smooth surface, each of the plurality of objects having a predetermined dimension capable of being found by the person with the normal tactile sensory ability when the person with the normal tactile sensory ability rubs a plantar pad of a finger or toe over the smooth surface of the substrate, each of the plurality of objects on the smooth surface having characteristics that prevent or make it difficult to visually locate the objects, each of the plurality of objects further having a different dimension corresponding to distinct levels of tactile sensory ability for use in determining the tactile sensory deficit of the test subject; and
a computer system, including:
  a data input device to receive input regarding which of the plurality of objects are sensed by a subject;
  a memory; and
  a processor adapted to communicate with the data input device and the memory to store inputted data regarding which of the plurality of objects are sensed by the subject in the memory and provide an objective grade of tactile sensory deficit.

22. The system of claim 21, wherein the processor is adapted to store inputted data regarding tactile sensory deficit for a plurality of subjects in a subject population, modify the normal tactile sensory ability for the subject population, and provide the objective grade of tactile sensory deficit based on the modified normal tactile sensory ability.

23. The system of claim 21, wherein the processor is adapted to trend the objective grades of tactile sensory deficit for the subject.

24. The system of claim 21, wherein the data input device for the computer system is the substrate or the substrate is an overlay to the data input device for the computer system.

25. The system of claim 21, wherein the processor is adapted to perform a statistical analysis on the inputted data to: identify a population that has been exposed to a nerve toxin, monitor an efficacy of a prophylactic or therapeutic treatment, or identify whether the sensory deficit is attributable to a localized nerve injury.

* * * * *

UNITED STATES PATENT AND TRADEMARK OFFICE
CERTIFICATE OF CORRECTION

| | | |
|---|---|---|
| PATENT NO. | : 8,133,189 B2 | Page 1 of 1 |
| APPLICATION NO. | : 12/030763 | |
| DATED | : March 13, 2012 | |
| INVENTOR(S) | : William R. Kennedy | |

It is certified that error appears in the above-identified patent and that said Letters Patent is hereby corrected as shown below:

On the title page, item (74), in "Attorney, Agent or Firm", in column 2, line 2, delete "Woessner, P.A." and insert -- & Woessner, P.A. --, therefor.

In column 5, line 36, delete "Pacininian" and insert -- Pacinian --, therefor.

In column 6, line 13, delete "(550 pm" and insert -- (550 μm --, therefor.

In column 15, line 5, in Claim 18, after "on" delete "using".

Signed and Sealed this
Nineteenth Day of June, 2012

David J. Kappos
*Director of the United States Patent and Trademark Office*